United States Patent
Sabnis et al.

(10) Patent No.: US 6,893,652 B2
(45) Date of Patent: May 17, 2005

(54) ENDOPARASITICIDAL GEL COMPOSITION

(75) Inventors: Shobhan S. Sabnis, Pennington, NJ (US); Jon Hayes, East Brunswick, NJ (US); Jack A. Zupan, Yardley, PA (US)

(73) Assignee: Wyeth, Madison, NJ (US)

( * ) Notice: Subject to any disclaimer, the term of this patent is extended or adjusted under 35 U.S.C. 154(b) by 32 days.

(21) Appl. No.: 10/202,552

(22) Filed: Jul. 24, 2002

(65) Prior Publication Data

US 2003/0096822 A1 May 22, 2003

Related U.S. Application Data

(60) Provisional application No. 60/315,104, filed on Aug. 27, 2001.

(51) Int. Cl.$^7$ ................................. A01N 25/24
(52) U.S. Cl. ................. 424/407; 424/405; 424/484; 514/30; 514/250
(58) Field of Search ................. 424/405, 484, 424/442, 407; 514/30, 280

(56) References Cited

U.S. PATENT DOCUMENTS

| | | | |
|---|---|---|---|
| 5,006,545 A | 4/1991 | Sarkozy et al. | |
| 5,536,715 A | 7/1996 | Hood | |
| 5,824,653 A | 10/1998 | Beuvry et al. | |
| 6,129,949 A | * 10/2000 | Schwertfeger et al. | ...... 427/220 |
| 6,165,987 A | 12/2000 | Harvey | |
| 6,340,672 B1 | * 1/2002 | Mihalik | ...... 514/30 |
| 2003/0236203 A1 | 12/2003 | Freehauf et al. | |

FOREIGN PATENT DOCUMENTS

| | | |
|---|---|---|
| EP | 0 717 993 A2 | 6/1996 |
| GB | 2 252 730 A | 8/1992 |
| HU | 207 944 B | 10/1990 |
| WO | WO2204/000034 A2 | 12/2003 |

* cited by examiner

*Primary Examiner*—Neil S. Levy
(74) *Attorney, Agent, or Firm*—Barbara L. Renda; Anne M. Rosenblum

(57) ABSTRACT

A homogenous, clear, veterinary gel composition which has a broad spectrum of efficacy against endoparasites over a prolonged period of time and which allows for higher concentrations of a mixture of parasiticidal agents in a single application. This composition is useful for treating and controlling endoparasiticidal infection and infestation in a homeothermic animal.

11 Claims, No Drawings

ENDOPARASITICIDAL GEL COMPOSITION

This application claims priority from copending provisional application Ser. No. 60/315,104, filed on Aug. 27, 2001, the entire disclosure of which is hereby incorporated by reference.

BACKGROUND OF THE INVENTION

Endoparasiticidal infection and infestation of homeothermic farm and companion animals are the cause of significant distress and economic loss to pet owners, animal husbandry men and the like. Efficient control of said parasites is, therefore, highly desirable and may be achieved by the administration of suitable endoparasiticidal agents, such as moxidectin and praziquantel.

Moxidectin is a second-generation endectocide of the milbemycin family of macrocyclic lactone compounds. The compound is registered and marketed in various formulations for the control of internal and external parasites in farm livestock and companion animals, including horses. A 2% oral gel formulation (EQUEST, QUEST) for horses is marketed worldwide. The product is highly effective against a broad-spectrum of internal parasites found in horses and ponies.

Equine tapeworms are commonly found in horses throughout the world. Prevalence does not appear to be related to breed or age. The most common species found in surveys has been *Anoplocephala perfoliata*, with fewer reports involving *A. magna* and *Paranoplocephala mamillana*. Until recently the horse tapeworm has been considered to be a relatively harmless inhabitant of the equine gastrointestinal tract. However, recent research has suggested that heavy burdens may predispose horses to various types of colic, and that the risk increases with the number of tapeworms present.

Moxidectin, in common with other macrocyclic lactones, does not have activity against cestodes, and an alternative class of anthelmintic, such as pyrantel or praziquantel is required for the control of equine tapeworm. Pyrantel is effective when given at double the dose normally recommended for control of G.I. nematodes. Praziquantel is an anthelmintic belonging to the pyrazinoisoquinolene class of compounds. It is effective against cestode and trematode infections in animals and humans. Praziquantel is registered in Australia for the control of tapeworm infections in horses at a dosage of 2.5 mg/kg bodyweight.

Modern endoparasiticidal agents, such as moxidectin and praziquantel, have a wide margin of safety, considerable activity against immature or larval stages of parasites and a broad spectrum of activity. Nonetheless, the usefulness of any endoparasiticidal agent is limited by the inherent efficacy of the drug itself, its mechanism of action, its pharmacokinetic properties, features relating to the host animal, features relating to the target parasites and the form of administration.

The "ideal" endoparasiticidal administrative form should have a broad spectrum of activity against mature and immature parasites, be easy to administer to a large number of animals, have a wide margin of safety, be compatible with other compounds, not require long withholding periods because of residues and be economical. Anthelminthic compositions for equidae are described in U.S. Pat. No. 5,824,653; however, said compositions are limited in their concentration of effective agents, hence requiring multiple doses for efficacious results. Anthelminthic formulations are also described in U.S. Pat. No. 6,165,987; however, these formulations suitable for oral administration are limited to pastes which may make visual identification of contaminants and accurate administration of measured dosages difficult.

Therefore, it is an object of this invention to provide an endoparasiticidal gel composition which is homogeneous and clear and which allows higher concentrations of anthelminthic or parasiticidal agents than formulations known heretofore.

It is another object of this invention to provide a method for the treatment and control of endoparasiticidal infection and infestation in homeothermic animals which gives an earlier onset of protection for a more prolonged period of time in comparison to formulations known heretofore.

These and other features, objects and advantages of the present invention will be apparent to those skilled in the art from the detailed description set forth hereinbelow, and from the appended claims.

SUMMARY OF THE INVENTION

The present invention provides an endoparasiticidal gel composition which comprises: about 1.0% to 3.5% wt/wt of moxidectin; about 10.0% to 15.0% wt/wt of praziquantel; about 4.0% to 24.0% wt/wt of benzyl alcohol; about 1.0% to 34.0% wt/wt of ethanol; about 2.0% to 15.0% wt/wt colloidal silicon dioxide; about 1.0% to 20.0% wt/wt surfactant and about 35.0% to 61.0% wt/wt of an oil.

The present invention further provides a method for the treatment and control of endoparasiticidal infection and infestation in a homeothermic animal and a method for the preparation of an endoparasiticidal gel composition.

DETAILED DESCRIPTION OF THE INVENTION

Endoparasiticidal agents such as moxidectin and praziquantel may be administered orally in the form of feed concentrates, feed additives, tablets, oblets, boluses, gels, pastes, or the like or may be administered parenterally as an injectable. Of the above-mentioned formulation types, arguably the most suitable for ease of administration, efficient and effective dosage, and economic and practical application of the endoparasiticidal agents moxidectin and praziquantel is an oral gel or paste. Feed additives and feed concetrates are unsuitable due to the lack of stability of said endoparasiticidal agents. Tablets, boluses, oblets and drenches are cumbersome to administer to large numbers of animals effectively and parenteral injection is more stressful for the animal and the handler.

A clear, easy-to-use gel form is preferable to a paste because it is easier on both animals and animal handlers, contamination is readily visible and the physical state of the gel readily converts to a liquid upon application of shear or increased temperature. This change from gel to liquid aides in the rapid breakup of the oral gel in the animal's mouth upon its insertion into the oral cavity. This process enables the easy transit of the dosage form from mouth to the gastrointestinal track., i.e., the product is readily swallowed. In contrast, paste formulations retain their structure and are often spit out of the animal's mouth. Trials in the field have demonstrated that animals treated with an active ingredient in gel form exhibit none of the signs of distaste and discomfort, such as head-throwing, tongue-rolling, spitting or not eating, which are characteristic of animals treated with an active ingredient in a paste form.

Surprisingly, it has now been found that moxidectin and praziquantel may be formulated in a clear, homogenous gel composition. The endoparasiticidal gel composition of the invention comprises about 1.0% to 3.5%, preferably about 1.5% to 2.5%, more preferably about 1.9% to 2.0% wt/wt of moxidectin; about 10% to 15%, preferably about 12.0% to 13.0%, more preferably about 12.0–12.5% wt/wt of praziquantel; about 4.0% to 24.0%, preferably 18.0% to 22.0%, more preferably about 22.0% wt/wt benzyl alcohol; about 1.0% to 34.0%, preferably about 5.0% to 7.5% wt/wt of ethanol; about 2.0% to 15.0%, preferably about 6.5% to 8.5% wt/wt of colloidal silicon dioxide; about 1.0% to 20.0%, more preferably about 3.0% to 6.0% wt/wt of a surfactant; and about 35.0% to 61.0%, more preferably about 42.0% to 48.0% wt/wt of an oil.

Optional components which may be present in the inventive composition include preservatives such as butylated hydroxytoluene, butylated hydroxyanisole, sorbic acid, 2-hydroxy-biphenyl, or the like, preferably butylated hydroxytoluene; thickeners such as ethyl cellulose, xanthum gum, carageenan, hydroxypropylcellulose, hydroxypropylmethylcellulose, or the like, preferably ethyl cellulose; or any conventional inert excipient commonly used in animal health compositions.

Surfactants suitable for use in the inventive composition include non-ionic surfactants such as polyoxyethylene sorbitan esters, preferably polysorbate 80, polyethylene glycol 660 hydroxystearate, polyoxyl 35 castor oil, or the like, preferably a polyoxyethylene sorbitan ester, more preferably polysorbate 80.

Oils suitable for use in the inventive composition include propylene glycol dicaprylate/dicaprate, caprylic/capric triglyceride or the like, preferably propylene glycol dicaprylate/dicaprate.

Advantageously, the clear, homogenous, endoparasiticidal gel composition of the invention ensures complete and accurate dosing with less stress for both the animal and the animal handler. Further, the inventive gel composition allows for higher concentrations of active ingredients, thereby minimizing the need for multiple dosing. Accordingly, the present invention provides a method for the treatment and control of endoparasiticidal infection and infestation in a homeothermic animal which comprises orally administering to said animal an effective amount of a gel composition which comprises: about 1.5% to 3.5% wt/wt of moxidectin; about 10.0% to 15.0% wt/wt of praziquantel; about 4.0% to 24.0% wt/wt of benzyl alcohol; about 1.0% to 34.0% wt/wt of ethanol; about 2.0% to 15.0% wt/wt of colloidal silicon dioxide; about 1.0% to 20.0% wt/wt of a surfactant; and about 35.0% to 61.0% wt/wt of an oil.

Effective amounts may vary according to the general health of the animal, the degree of infection or infestation, the parasite species, the age of the animal, the organs infected or infested, or the like. In general, amounts of said gel composition sufficient to provide about 0.3 mg/kg to 0.5 mg/kg, preferably about 0.4 mg/kg of moxidectin per body weight of the animal and about 2.0 mg/kg to 3.0 mg/kg, preferably about 2.5 mg/kg of praziquantel per body weight of the animal are suitable.

Homeothermic animals suitable for treatment in the method of invention include equine, bovine, ovine, swine, caprine, canine, feline or the like animals, preferably equine animals, more preferably horses.

The present invention also provides a method for the preparation of a endoparasiticidal gel composition which comprises one or more of the following steps:

1) dissolving a thickener, such as ethyl cellulose, in a mixture of benzyl alcohol and ethanol to form a solution A;

2) suspending praziquantel in an oil, such as propylene glycol dicaprylate/dicaprate which has been preheated to about 80° C., to form a suspension B;

3) admixing solution A with suspension B at temperatures ≦50° C. until a solution C which is homogenous at room temperature is obtained;

4) admixing surfactant and optionally butylated hydroxytoluene with solution C to form solution D;

5) sequentially admixing moxidectin and colloidal silicon dioxide to solution D to form gel E; and 6) mixing gel E under a vacuum to form a clear yellow endoparasiticidal gel composition that is essentially free of air.

Several preferred embodiments of the present invention are set forth in the following examples. These examples are merely illustrative and are not intended to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the present invention, and the appended claims.

EXAMPLE 1

Preparation of Endoparasiticidal Gel Composition A

| Component Description | % wt/wt |
| --- | --- |
| moxidectin, 90% potency | 1.95 |
| praziquantel, 100% potency | 12.17 |
| benzyl alcohol | 22.00 |
| butylated hydroxytoluene | 0.08 |
| polysorbate 80[1] | 5.00 |
| colloidal silicon dioxide | 7.50 |
| ethyl cellulose (visc. 4) | 0.25 |
| dehydrated alcohol, usp | 5.00 |
| Propylene glycol dicaprylate/dicaprate[2] | 45.84(q.s.[3]) |

[1]CRILLAT ® 4HP, manufactured by Croda Inc., Parsippany, NJ
[2]Miglyol ® 840, manufactured by Condea Vista, Cranford, NJ.
[3]quantity sufficient to bring total to 100% wt/wt.

Method of Preparation

Step 1. Ethyl cellulose is slowly dissolved in a mixture of benzyl alcohol and ethanol with stirring.

Step 2. Propylene glycol dicaprylate/dicaprate which has been preheated to 80° C. is slurried with praziquantel to form a suspension. When the temperature of the suspension is <50° C., the solution obtained in step 1 is added, stirring is continued until the praziquantel is dissolved and the resultant mixture is cooled to room temperature.

Step 3. Butylated hydroxytoluene and polysorbate 80 are added to the mixture obtained in Step 2 with continued stirring.

Step 4. Moxidectin is added to the mixture obtained in Step 3 with stirring.

Step 5. Colloidal silicon dioxide is added to the mixture obtained in step 4 and mixing under a vacuum using a suitable mixer is continued until a clear yellow gel, that is free of air, is formed.

EXAMPLE 2
Comparative Field Evaluation of Efficacy of Composition A

In this evaluation, horses with known strongyle infestation are treated orally with a dose of 0.4 mg/kg moxidectin and 2.5 mg/kg praziquantel gel (Composition A) or a dose of 0.2 mg/kg abamectin and 2.5 mg/kg praziquantel paste (EQUIMAX® manufactured by Virbac, New South Wales, Australia), or given no treatment (Control). Each treatment consists of 10 horses. Fecal egg counts (FEC) are performed and recorded at biweekly intervals post treatment. The data are averaged. The results are shown in Table I.

TABLE I

Comparative Evaluation

| Treatment | Fecal Egg Count[a] Weeks Post Treatment | | | | | | |
|---|---|---|---|---|---|---|---|
| | 2 | 4 | 6 | 8 | 10 | 12 | 14 |
| Comp. A | 0 | 0 | 26.7 | 61.9 | 173.8 | 321.0 | 178.0 |
| EQUI-MAX ® | 0 | 4 | 288.9 | 325.0 | 596.0 | 880.0 | 1140.0 |
| Control | 1246.7 | 891.1 | 773.3 | 1126.7 | 2257.8 | 2928.9 | —[b] |

[a]Arithmetic mean
[b]Controls treated

As can be seen from the data shown on Table I, the gel composition of the invention provides significantly increased efficacy for a greater period of time than a comparable commercially available paste composition.

EXAMPLE 3
Evaluation of the Endoparasiticidal Efficacy of Composition A

In this evaluation a group of 12 horses are treated orally with a dose of 0.4 mg/kg moxidectin and 2.5 mg/kg praziquantel (Composition A) and a group of 12 horses are left untreated (Control). Two weeks post treatment, parasite burdens are determined and % efficacy for treated animals is calculated. The data are averaged. The results are shown in Table II.

| Parasites | |
|---|---|
| Column Heading | Scientific Name |
| G. intest. | G. intestinalis |
| G. nasalis | G. nasalis |
| Paranopl. | Paranoplocchphila |
| Anoplo. Spp. | Anoplocephala Spp. |

TABLE II

Evaluation of Endoparasiticidal Efficacy

| | % Efficacy | | | |
|---|---|---|---|---|
| Treatment | G. intest. (12/12)[a] | G. nasalis (12/12) | Paranopl. (10/12) | Anoplo. Spp. (12/12) |
| Comp. A | 96.7 | 98.8 | 99.1 | 100.0 |
| Control[b] | 201.8 | 136.5 | 11.2 | 6.7 |

[a]Number infected/total
[b]Geometric means parasite (degree of infection)

As can be seen from the data on Table II, the gel composition of the invention demonstrates a high degree of efficacy over a broad spectrum of endoparasites.

EXAMPLE 4
Efficacy of Gel Formulation

Twenty-six New Forest cross male ponies approximately 1–2 years of age were used in this study. All were sourced from an area of the New Forest on which animals known to be infected with *Gasterophilus* spp. and *A. perfoliata* had grazed. This had been assessed by post-mortem examination of material at a horse abattoir in South West England carried out before the trial.

The horses were housed in small groups of 4–6 for 18 days prior to treatment. Each horse was given a physical examination by a veterinary surgeon to determine its suitability for use in the trial. Post-mortem examination of two randomly selected tracer animals seven days prior to treatment revealed moderate burdens of *P. mamillana* and *A. perfoliata*, as well as moderate to heavy burdens of both the L2 and L3 instars of *G. intestinalis* and *G. nasalis*.

The remaining 24 animals were ranked in order of increasing bodyweight, to form 12 pairs, then allocated at random to either untreated control or to moxidectin/praziquantel gel groups. The latter was administered at a rate of 0.5 ml/25 kg bodyweight to provide 0.4 mg moxidectin/kg and 2.5 mg praziquantel/kg bodyweight. Treatment consisted of a single oral administration into the back of the mouth at the base of the tongue. The animals were treated using pre-filled syringes graduated to the nearest 25 kg. The syringes were weighed before and after treatment to determine the actual dose given.

On days 13–14 post-treatment all animals were necropsied and their bot and tapeworm burdens determined. Faecal samples were collected 14 days prior to treatment and at time of necropsy on day 13–14 post-treatment and examined for the presence of tapeworm eggs and strongyle eggs using a modified McMaster flotation technique. At necropsy the gastrointestinal tract from stomach to large intestine was removed and divided by ligature into stomach, small intestine, caecum, ventral and dorsal colon, for separate processing.

*Gasterophilus* spp larvae present on the gastric mucosa and in the stomach contents were removed for enumeration. Identification of individual species and instar was carried out according to the key described in Wells and Knipling (1937).

Each section of the intestines was opened and the contents collected. Any visible tapeworms remaining on the intestinal wall were similarly removed for identification and counting. Identification of individual tapeworm species was carried out according to predilection site, size and other morphological features. A bulk faecal sample from the untreated control group collected at necropsy was cultured to identify the species/genus of nematode present.

Bot and tapeworm counts were transformed by Y=In (count+1) transformation prior to analysis. The two groups were compared using a two-way analysis of variance with the level of significance set at the 5% level. The moxidectin/praziquantel combination equine gel formulation was determined to have activity against a specific species of parasite if each of the following three conditions were met:
1. the efficacy equals or exceeds 90% as determined by the geometric mean;
2. at least six control animals are infected with the same parasite species; and
3. the treatment effect is significant at the P<0.05 level.

Results

No adverse effects were observed in any of the treated animals after treatment. The gel formulation also appeared to be palatable. Apart from one horse, which accidentally ingested twice the recommended dose through biting on the syringe, the actual dose administered ranged from 94 to 102 (mean 99) % of the target dose.

All 24 ponies had positive strongyle eggs counts prior to treatment. Egg counts ranged from 60–1050 with a mean of 252 eggs per gram (EPG). After treatment, the figures were 288 (range 0–980) epg for the controls and 0.3 epg (one positive animal) for the treated group, representing a reduction of 99.9%. Coproculture of pooled faeces from the control group at slaughter revealed that the strongyle population was composed of 68% *Cyathostoma* spp. and 32% *Strongylus* spp.

All 12 controls carried *A. perfoliata* burdens at necropsy, as shown in Table III. Numbers ranged from 1–36 with a geometric mean of 6.7. In contrast, the treated group had zero counts. Ten out of the 12 ponies were also infected with *P. mamillana* (mean 11.2, range 1 to 133), whereas in the treated group a single tapeworm was found in one animal only (mean 0.1) giving an efficacy figure of 99.9% (P<0.001). No *A. magna* were found in any of the horses. Faecal examination failed to detect any tapeworm eggs in any of the animals either before or after treatment. This reflects the lack of sensitivity of the McMaster flotation technique for determining the presence of tapeworm eggs in faeces.

All the control animals were found to be infected with *G. intestinalis* and *G. nasalis*. Both the L2 and L3 stages were present. For *G. intestinalis*, the numbers ranged from 13–278 (mean 91.9) and 2–312 (mean 89.4) respectively. Corresponding figures for the treated group were 0–24 (mean 2.3) and 0–17 (mean 3.9) giving % reduction figures of 97.5% (P<0.001) and 95.6% (P<0.001) for the L2 and L3 stages respectively. The numbers of *G. nasalis* in the controls ranged from 12–400 (mean 46.7) for L2 and 25–140 (mean 80.8) for L3. In the treated group the figures were 0–10 (mean 1.4) and 0–8 (mean 0.3) giving 97% (P<0.001) and 99.6% (P<0.001) efficacy against the L2 and L3 stages respectively.

The results of this study confirm that moxidectin/praziquantel equine gel at 0.4 mg moxidectin/kg and 2.5 mg praziquantel/kg bodyweight is highly effective against tapeworms and bots in naturally infected horses in the UK. It was 99–100% effective against *A. perfoliata* and *P. mamillana* and 95.6–99.6% effective against the L2 and L3 instars of *G. intestinalis* and *G. nasalis*. The product was well tolerated and was accepted by the animals. The 99.9% reduction in strongyle faecal egg counts suggests that moxidectin, in conjunction with praziquantel, continues to have excellent activity against gastro-intestinal nematodes.

TABLE III

Mean Tapeworm and bot counts at Necropsy

|  | Control | Treated | % Efficacy |
|---|---|---|---|
| Number of Animals | 12 | 12 |  |
| A perfoliata | 6.7 | 0 | 100 |
|  | (1–36) | (—) |  |
| P. mamillana | 11.2 | 0.1 | 99.1 |
|  | (1–133) | (0–1) |  |
| G. intestinalis |  |  |  |
| L2 | 91.9 | 2.3 |  |
|  | (13–278) | (0–24) | 97.5 |
| L3 | 89.4 | 3.9 |  |
|  | (2–312) | (0–17) | 95.6 |

TABLE III-continued

Mean Tapeworm and bot counts at Necropsy

|  | Control | Treated | % Efficacy |
|---|---|---|---|
| G. nasalis |  |  |  |
| L2 | 46.7 | 1.4 |  |
|  | (12–400) | (0–10) | 97.0 |
| L3 | 80.8 | 0.3 |  |
|  | (25–140) | (0–8) | 99.6 |

EXAMPLE 5

A two part field study included a total of 43 horses for the nematode part (I) and another 8 horses for the tape worm part (II). Part I: Group A (N=26) was treated with the moxidectin/praziquantel gel, Group B (N=10) received an abamectin/praziquantel paste and 9 horses in Group C remained as an untreated control group. The efficacy was monitored by faecal egg per gram (epg) measurement: the average challenge in the Group C ranged from 773.3 to 2928.9 epg. When following a common recommendation to treat when 50% of horses in the group have epg≧200, the horses in Group B would have had to be treated between week 6 and 8, when 6 out of 8 horses sampled had epg≧200. Group A horses did not warrant a treatment at any time during the 14 week study period. Group C had to be treated at week 12 for animal welfare reasons. Efficacy against tapeworm was 100%. A safety study in 14 young foals from 3 weeks to 7 weeks of age showed moxidectin 2%/praziquantel 12.5% horse gel to be safe when applied up to 3 times recommended dose rate.

What is claimed is:

1. An endoparasiticidal gel composition which comprises: about 1.0% to 3.5% wt/wt of moxidectin; about 10.0% to 15.0% wt/wt of praziquantel; about 4.0% to 24.0% wt/wt of benzyl alcohol; about 1.0% to 34.0% wt/wt of ethanol; about 2.0% to 15.0% wt/wt of colloidal silicon dioxide; about 1.0% to 20.0% wt/wt of a surfactant; and about 35.0% to 61.0% wt/wt of an oil, wherein said composition is an oral gel.

2. The composition according to claim 1 wherein the oil is propylene glycol dicaprylate/dicaprate or dicaprylic/dicapric triglyceride.

3. The composition according to claim 1 wherein moxidectin is present at about 1.5% to 2.5% wt/wt.

4. The composition according to claim 1 wherein praziquantel is present at about 12.0% to 13.0% wt/wt.

5. The composition according to claim 1 wherein benzyl alcohol is present at about 18.0% to 22.0% wt/wt.

6. The composition according to claim 1 wherein ethanol is present at about 5.0% to 7.5% wt/wt.

7. The composition according to claim 5 wherein the surfactant is present at about 3.0% to 6.0%.

8. The composition according to claim 7 wherein the surfactant comprises a polyoxyethylene sorbitan ester.

9. The composition according to claim 8 wherein ethanol is present at about 5.0% to 7.5% wt/wt.

10. The composition according to claim 9 wherein the oil is propylene glycol dicaprylate/dicaprate.

11. The composition according to claim 10 wherein moxidectin is present at about 1.9% to 2.0% wt/wt and praziquantel is present at about 12.0% to 12.5% wt/wt.

* * * * *